United States Patent [19]
Terry et al.

[11] Patent Number: 5,336,187
[45] Date of Patent: Aug. 9, 1994

[54] AUTOMATIC COVER DISPOSABLE SYRINGE

[76] Inventors: Mark Terry, 1715 Monican St., Philadelphia, Pa. 19138; Harry G. Hughes, Jr., 15413 Birchwood Ave., Roslyn, Pa. 19001; Edward D. Williams, 1432 E. Washington La., Philadelphia, Pa. 19138

[21] Appl. No.: 80,307

[22] Filed: Jun. 24, 1993

[51] Int. Cl.⁵ ............................................. A61M 5/00
[52] U.S. Cl. ................................. 604/110; 604/198
[58] Field of Search ............. 604/110, 187, 192, 195, 604/198, 263, 218

[56] References Cited

U.S. PATENT DOCUMENTS

| | | | |
|---|---|---|---|
| 5,064,419 | 11/1991 | Gaarde | 604/195 |
| 5,163,908 | 11/1992 | Lambert | 604/110 |
| 5,211,629 | 5/1993 | Pressly et al. | 604/110 |

*Primary Examiner*—John D. Yasko
*Attorney, Agent, or Firm*—David Edwards

[57] ABSTRACT

An accident-proof syringe that has an automatically and permanently covered needle point at all times for use with clinical apparatus operably applied to a patient by way of skin puncture; this disposable non-reusable hypodermic needle assembly comprises a hollow syringe body, a piston slidably mounted inside the syringe body and defining between the closed end of the syringe body and the piston a compartment for containing a liquid to be injected or withdrawn from a person, an injection needle, the base of which is fastened to a needle support member, said support member and said piston being adapted for allowing at least partial insertion of said support member in said piston and for allowing the needle to communicate with said syringe body compartment upon said insertion, a substantially cylindrical sleeve member which is open at both ends, said needle support member being mounted at one end portion of said sleeve member, retaining means for fastening said sleeve member to the syringe body during the storage of the hypodermic needle assembly and at least until the beginning of the injection, a substantially cylindrical, inter- protective sheath member for protecting the needle, and a collapsible bellow shaped inner needle shaft cover that surrounds a portion of the needle and abuts at one end against said needle support member and at its other end against said protective sheath member to urge the protective sheath into a rest position where said sheath member protrudes outside said sleeve member and surrounds the needle tip.

7 Claims, 1 Drawing Sheet

AUTOMATIC COVER DISPOSABLE SYRINGE

BACKGROUND OF THE INVENTION

This invention relates to the a disposable hypodermic syringe that has a protective sleeve over the needle.

Prior to the present invention, the incidence of contracting deadly diseases through needle stick injuries had greatly increased in the medical industry. Any needle, once it has contacted blood, is a potentially lethal instrument. Accidental needle stick injuries are the main cause of occupationally acquired Hepatitis B, HIV, and other infections. Such injuries occur, all too often, both during use and after disposal of needles.

The spread of Hepatitis B and HIV among the patient population has highlighted the serious implications of needle stick injuries. Healthcare personnel, particularly those working in high risk areas (i.e., Hematology, Casualty, intensive care, sexually transmitted diseases, Renal, etc.) need protection from potential infection and consequent anxiety. Hospital management has a statutory duty to protect its staff against occupational hazards and need to reduce the cost of post needle-stick testing and potential liability.

Devices intended to make the manual resheathing of needles safer are no answer; this type of device will not protect the user during needle use or against careless disposal. What is needed is a new safety needle that automatically and permanently covers the needle point before use and as soon as it is withdrawn from the patient: an accident-proof needle.

U.S. Pat. Nos. 4,936,830 and 4,813,940 disclose disposable hypodermic syringes that have an automatic covering device for the needle after use. U.S. Pat. No. 4,826,490 also disclose a disposable hypodermic syringe that has a slidable sleeve that is manually slidable over a contaminated needle. None of this prior art discloses the instant invention.

SUMMARY OF THE INVENTION

The present invention is directed to an accident-proof syringe that has an automatically and permanently covered needle point at all times for use with clinical apparatus operably applied to a patient by way of skin puncture; this disposable non-reusable hypodermic needle assembly comprises
a) a hollow syringe body closed at one of its ends and open at the other end,
b) a piston slidably mounted inside the syringe body and defining between the closed end of the syringe body and the piston a compartment for containing a liquid to be injected or withdrawn from a person,
c) an injection needle, the base of which is fastened to a needle support member, said support member and said piston being adapted for allowing at least partial insertion of said support member in said piston and for allowing the needle to communicate with said syringe body compartment upon said insertion,
d) a substantially cylindrical sleeve member which is open at both ends, said needle support member being mounted at one end portion of said sleeve member,
e) retaining means for fastening said sleeve member to the syringe body during the storage of the hypodermic needle assembly and at least until the beginning of the injection,
f) a substantially cylindrical, inter- protective sheath member for protecting the needle, said sheath member being closely adjacent the needle having a small opening at its forward end approximate size of the needle completely surrounding the needle with the tip of the needle being completely inside the sheath member when the needle is not in use and extending through forward opening of said sleeve member while the other end of said sheath member is supported by support means in the sleeve and is slidably engaged with the sleeve, and
g) a collapsible bellow shaped inner needle shaft cover that surrounds a portion of the needle and abuts at one end against said needle support member and at its other end against said protective sheath member to urge the protective sheath into a rest position where said sheath member protrudes outside said sleeve member and surrounds the needle tip.

BRIEF DESCRIPTION OF THE DRAWINGS

In order that the invention may be more fully understood, reference will now be made, by way of example, to the accompanying drawings, in which.

DETAILED DESCRIPTION OF THE INVENTION

Figure 1:
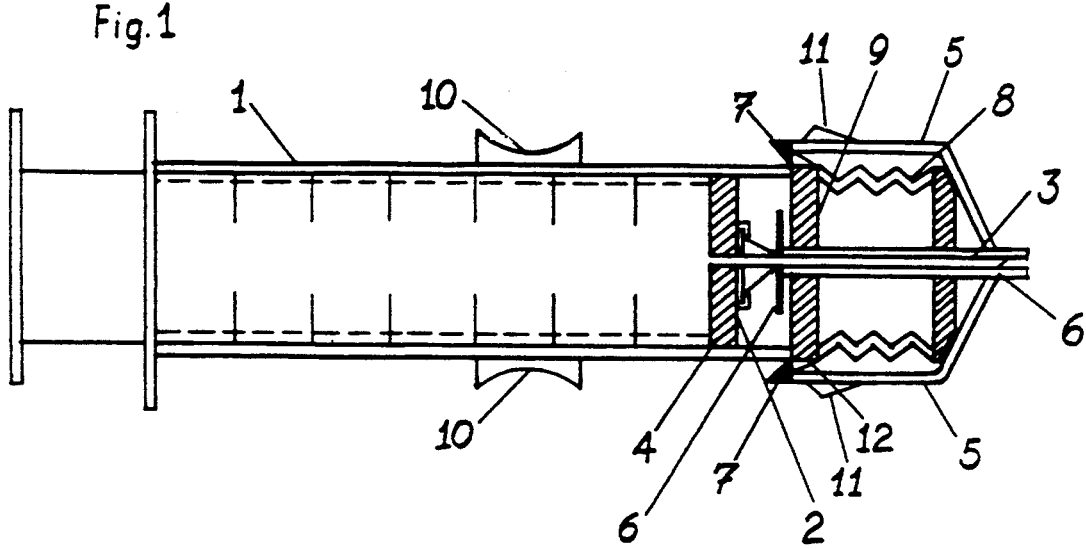
FIG. 1 is a sectional view of the invention in the normal position of the device.

Referring to FIG. 1, the syringe comprises a cylindrical hollow syringe body 1, which is open at one of its ends and closed at the other end to form a compartment of the liquid substance to be injected or withdrawn from a person. The syringe body 1 is advantageously made from a glass tube, but could, of course, be made from any other suitable material, for example, a metal or a plastic material.

A piston 2 is mounted inside the syringe body 1 for low friction sliding engagement of its outer side wall (or sealing means fastened thereto) with the inner wall of the syringe body 1, while maintaining the tightness of the above mentioned compartment defined by the syringe body and the back wall of the piston 2 facing the closed end of the syringe body.

An injection needle 3 is supported with its tip pointing in the direction opposite to that of the closed end of the syringe body 1 and its rear end held in a substantially cylindrical support member 4 which maintains the needle base aligned with the axis of the syringe body 1. The rear end of the needle 3 communicates with the compartment containing the substance to be injected, by way of a passage extending through the piston 2. More specifically, the support member 4 of the needle has a cylindrical portion inserted in and extending axially through the piston 2, which portion contains a channel, for example, the channel of the needle itself, constituting said passage.

Figure 3:
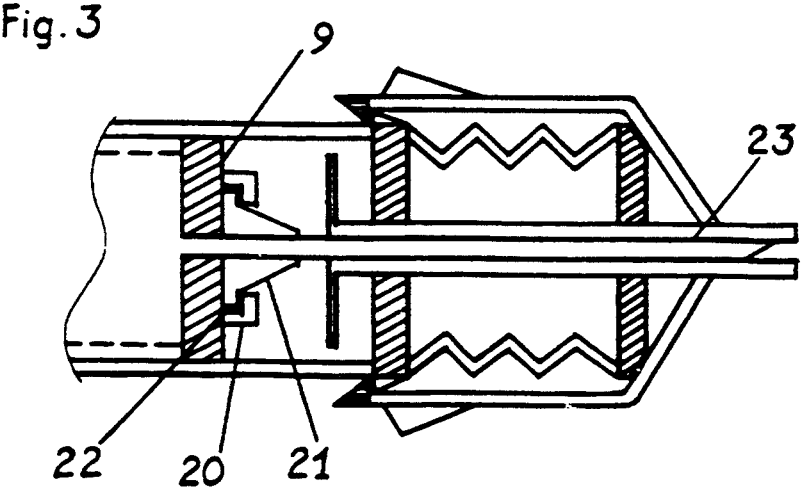
FIG. 3 is a sectional view of an embodiment of the needle attachment to the syringe body.

The needle 3 can be attached to the base 4 by either being molded or extruded therein when the base 4 is being manufactured or it can be attached by a screwing locking mechanism as shown in FIG. 3. A standard luer lock needle tip is used in this syringe design. In this type of attachment, a female portion 20 is molded or secured in the base 9 and a needle 23 with integral base 21 with threads 22 thereon is screwed in place in the female portion 20.

A cylindrical sleeve 5 is open at both ends and has an outer diameter slightly bigger than the outer diameter of the syringe body 1 at one end and a smaller diameter slightly bigger than the needle at the other end (or forward end); the smaller diameter end of sleeve 5 has a slanted portion with a hole at the apex; the needle is positioned at this smaller diameter end, in the initial storage position shown in FIG. 1, with its bigger end located outside and slidably connected to the body 1. Retaining means 7 is a stop that prevents the protective covering or sleeve 5 from being pulled away from (or off) the syringe body 1. Retaining means 7 interlocks with stop 12 on the syringe body 1. Retaining means 7 is either an integral part of sleeve 5 or can be a piece of rubber or resilient plastic material that is attached to the sleeve 5 by various means for achieving the purpose such as by gluing, riveting, etc. Likewise, the stop 12 that reacts with retaining means 7 can also be an integral part of the body 1 by extruding or forming the stop in the material at the time the body is made or it can be added later from a piece of rubber or resilient plastic material that is attached to the body 1 by gluing, riveting, etc. The sleeve 5 has this retaining means or lip 7 on its inside edge of the sleeve 5 to engage the peripherally mounted stop 12 to stop the forward motion of the sleeve 5 when the needle is removed from the patient or is being automatically stored.

A concentric bellow 8 working under compression surrounds the needle 3, with one end of the bellow 8 abutting against the support member 9 and the other end against the inner face of the slanted end portion of the sleeve 5 so as to urge the sleeve 5 automatically to the closed position as shown in FIG. 1. In this position, the inside of the sleeve 5 is practically tight against the outside, and the exerted force on the bellow 8 is sufficient to prevent the needle 3 from coming out of the protective end wall of the sleeve 5 under normal conditions before the syringe is used. The support member 9 comprises a front portion disposed inside the sleeve 5 and fastened thereto. The bellow 8 is composed of a material that is more pliable that the syringe itself so that it operates like an accordion but has strength to urge the sleeve 5 to the protective position for the needle automatically when not in use. In other words, an effort must be made to use the needle by exerting force on the protective sleeve 5 to expose the needle; but once the needle has been used and the force released, the protective sleeve 5 will automatically reposition itself to the protective position in the absence of any external force to the contrary.

In order to prevent damaging the needle 3 and to stop the backward movement of the bellow 8, inter-protective sheath 6 forms a concentric housing with the sleeve 5 for the needle; the sheath 6 is cylindrical in shape that is only slightly bigger in diameter than the needle 3, thus being closely adjacent to the needle 3; one of the ends of the inter-protective sheath 6 has a flared foot that will stop at the base, thus preventing excessive exposure of or damage to the needle 3 while the other end is open and protrudes through the sleeve 5 for exposing the needle when necessary. In other words, the inter-protective sheath prevents the needle 3 from being broken and stops backward movement of the bellows 8. This inter-protective sheath 6 can be an integral part of the sleeve 5 or can be welded or glued or attached by any means that would be well known in the art.

Figure 2:
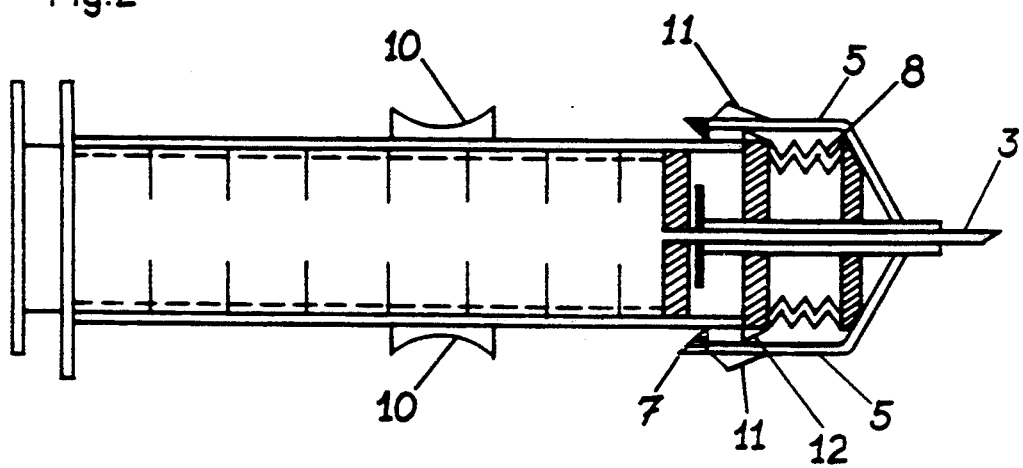
FIG. 2 is a sectional view of the invention with the sheath retracted to expose the needle.

This syringe can be automatically or manually operated. FIG. 2 shows the syringe in the retracted position of the needle. If the sleeve is retracted manually, finger grip 10 is needed to hold the BARREL of the syringe 1 with one hand while the other hand grips finger tabs 11 on sleeve 5 and manually move the sleeve 5 up on the syringe 1 to exposed the needle. When the finger tabs 11 are let go, the pressure exerted on the sleeve by the bellow 8 will move the sleeve 5 downwardly to cover the needle 3.

In an automatic operation mode, pressure is applied on the sleeve 5 when an injection or withdrawal is about to be made up against the patient or apparatus; this pressure will be sufficient to make the sleeve retract enough to expose and simultaneously use the needle. The bellow 8 will be in the fully compressed position as shown is FIG. 2. It should be noted that during the penetration of the needle 3, the needle 3 is perfectly well guided in the axial direction, by the housing of the inter protective sheath 6. When the needle is removed from the subject or apparatus, the sleeve automatically covers the needle again and thus will prevent needle sticks inadvertently. This is accomplished by the bellow expanding to push the protective sleeve 5 from the outside of the body 1 into the position covering the needle. The extent of the forward and backward movements of the sleeve 5 required in an injection cycle is automatically varied depending on the intended use and method of operation of the syringe.

A person using the syringe can use one hand to operate the needle without having to exert an extraordinary amount of force but the force of the bellow is sufficient so that the needle is automatically and rapidly covered when disengaged to prevent any exposure to danger of needle sticks; this system eliminates any risk of accidental pricking. In other words, the force exerted by the bellow 8 is adequate to prevent the protective sleeve 5 from being removed from the tip of the needle just by careless or reckless handling of the syringe. It takes a conscious effort to remove the protective sleeve.

What is claimed is:

1. An accident-proof, disposable, non-reusable, hypodermic needle syringe assembly that has an automatically and permanently covered needle point at all times for use with clinical apparatus operably applied to a patient by way of skin puncture comprising
   a) a hollow syringe body closed at one of its ends and open at the other end,
   b) a piston slidably mounted inside the syringe body and defining between the closed end of the syringe body and the piston a compartment for containing a liquid to be injected or withdrawn from a person,
   c) an injection needle, the base of which is fastened to a needle support member, said support member and said piston being adapted for allowing at least partial insertion of said support member in said piston and for allowing the needle to communicate with said syringe body compartment upon said insertion,
   d) a substantially cylindrical sleeve member which is open at both ends, said needle support member being mounted at one end portion of said sleeve member,
   e) retaining means for fastening said sleeve member to the syringe body during the storage of the hypodermic needle assembly and at least until the beginning of the injection,
   f) a substantially cylindrical, inter- protective sheath member for protecting the needle, said sheath member being closely adjacent to the needle having a small opening at its forward end approximate size of the needle completely surrounding the needle with the tip of the needle being completely inside the sheath member when the needle is not in use while the other end of said sheath member is supported by support means in the sleeve and is slidably engaged with the sleeve, and g) a collapsible bellow shaped inner needle shaft cover that surrounds a portion of the needle and abuts at one end against said needle support member and at its other end against said protective sheath member to urge the protective sheath into a rest position where said sheath member protrudes outside said sleeve member and surrounds the needle tip.

2. The syringe assembly of claim 1, wherein the needle is molded in the base.

3. The syringe assembly of claim 1, wherein the needle is attached to the base by a screwing locking mechanism.

4. The syringe assembly of claim 1, wherein the inter-protective sheath has a flared foot thereon for stopping backward MOTION of the bellow.

5. The syringe assembly of claim 1, wherein the syringe is made of glass or a plastic material.

6. The syringe assembly of claim 1, wherein the syringe body has finger grips thereon for an operator to hold the BARREL of the syringe during use thereof.

7. The syringe assembly of claim 6, wherein the sleeve has finger tabs thereon so that the operator can use his other hand for manually operating the syringe in concert with the finger grips.

* * * * *